United States Patent
Kim et al.

(10) Patent No.: US 8,319,007 B2
(45) Date of Patent: Nov. 27, 2012

(54) MOUSE MODELS WITH ENHANCED ESSENTIAL TREMOR AND PREPARATION METHOD THEREOF

(75) Inventors: Daesoo Kim, Daejeon (KR); Ki Young Chang, Daejeon (KR); Hyeyeon Park, Seoul (KR); Young Gyun Park, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 163 days.

(21) Appl. No.: 12/755,851

(22) Filed: Apr. 7, 2010

(65) Prior Publication Data

US 2010/0263063 A1 Oct. 14, 2010

(30) Foreign Application Priority Data

Apr. 13, 2009 (KR) .................. 10-2009-0031857

(51) Int. Cl.
G01N 33/00 (2006.01)
A01K 67/00 (2006.01)
A01K 67/027 (2006.01)
C12N 15/00 (2006.01)

(52) U.S. Cl. .................. 800/3; 800/13; 800/14; 800/18; 800/22

(58) Field of Classification Search ................ 800/3, 13, 800/14, 18, 22
See application file for complete search history.

(56) References Cited

U.S. PATENT DOCUMENTS

2003/0106083 A1* 6/2003 Allen

OTHER PUBLICATIONS

Zeller et al., 2008, Molecular Pharmacology, vol. 73, p. 282-291.*
Tsien et al. "Calcium Channels in Excitable Cell Membranes," *Ann. Rev. Physiol.*, vol. 45:341-358 (1983).
Tsien et al., "Reflections on $Ca^{2+}$-channel diversity, 1988-1994," *Trends Neurosci.*, vol. 18(2):52-54 (1995).
Mohler et al. "Heterogeneity of $GABA_A$-Receptors: Cell-Specific Expression, Pharmacology, and Regulation," *Neurochemical Research*, vol. 20(5):631-636 (1995).
Vicini et al. "$GABA_A$ Receptor α1 Subunit Deletion Prevents Developmental Changes of Inhibitory Synaptic Currents in Cerebellar Neurons," *The Journal of Neuroscience*, vol. 21(9):3009-3016 (2001).
Kim et al. "Lack of the Burst Firing of Thalamocortical Relay Neurons and Resistance to Absence Seizures in Mice Lacking $α_{1G}$ T-Type $Ca^{2+}$ Channels," *Neuron*, vol. 31:35-45 (2001).
Perez-Reyes "Molecular Physiology of Low-Voltage-Activated T-type Calcium Channels," *Physiol. Rev.*, vol. 83:117-161 (2003).
Kim et al. "Thalamic Control of Visceral Nociception Mediated by T-Type $Ca^{2+}$ Channels," *Science*, vol. 302:117-119 (2003).
Kralic et al. "Genetic essential tremor in γ-aminobutyric $acid_A$ receptor α1 subunit knockout mice," *The Journal of Clinical Investigation*, vol. 115(3):774-779 (2005).

* cited by examiner

*Primary Examiner* — Shin-Lin Chen
(74) *Attorney, Agent, or Firm* — Klarquist Sparkman, LLP.

(57) ABSTRACT

Disclosed herein are an α1/CaV3.1 double knockout mouse or $α1^{-/-}$; Emx1-Cre mouse with enhanced essential tremor and a screening method of therapeutic agents for essential tremor by using the same. The α1/CaV3.1 double knockout mouse or $α1^{-/-}$; Emx1-Cre mouse of the present invention may be usefully used for development of therapeutic agents for essential tremor because the mouse exhibits essential tremor strong and evident enough to be visually confirmed, compared to an α1 knockout mouse.

3 Claims, 4 Drawing Sheets

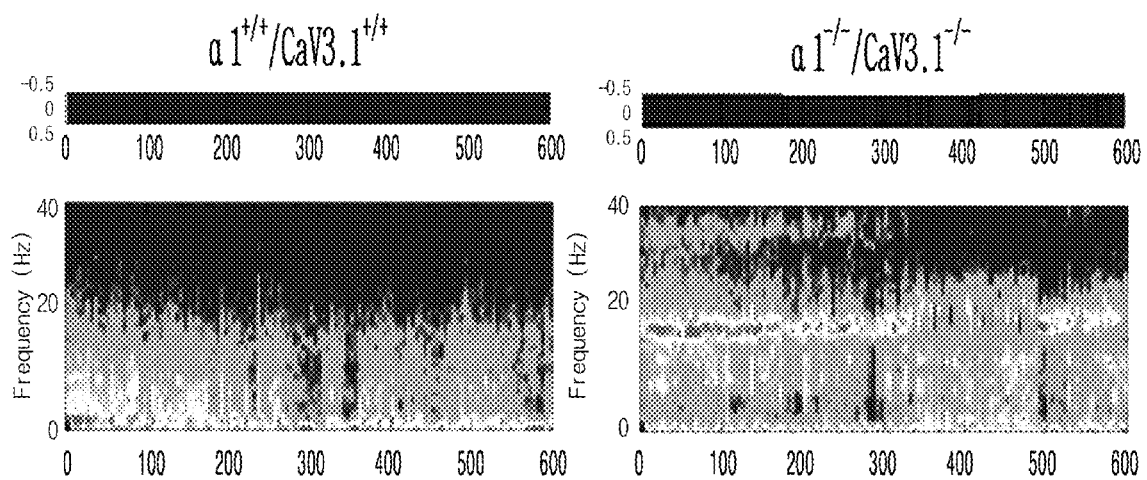
[Fig.1]

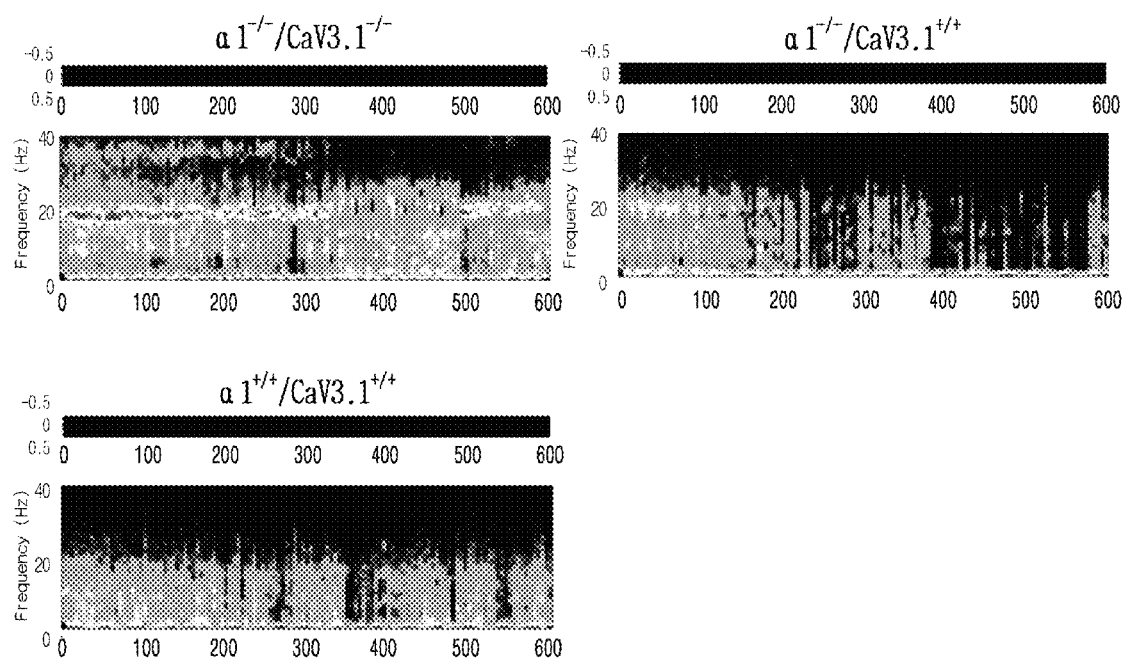

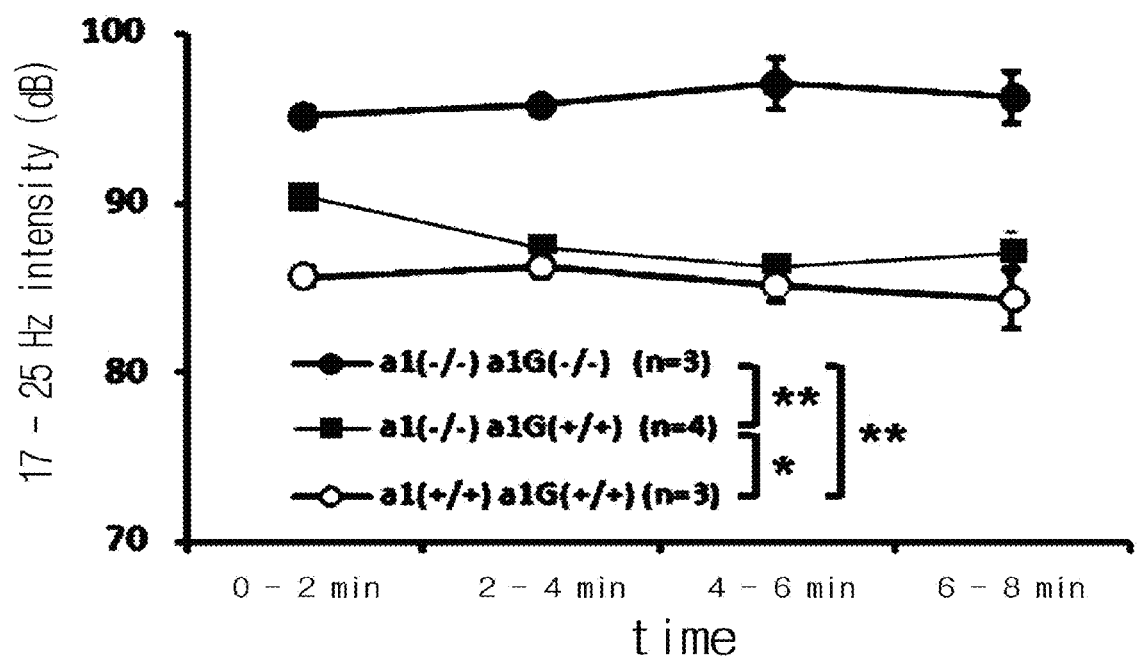
[Fig. 3]

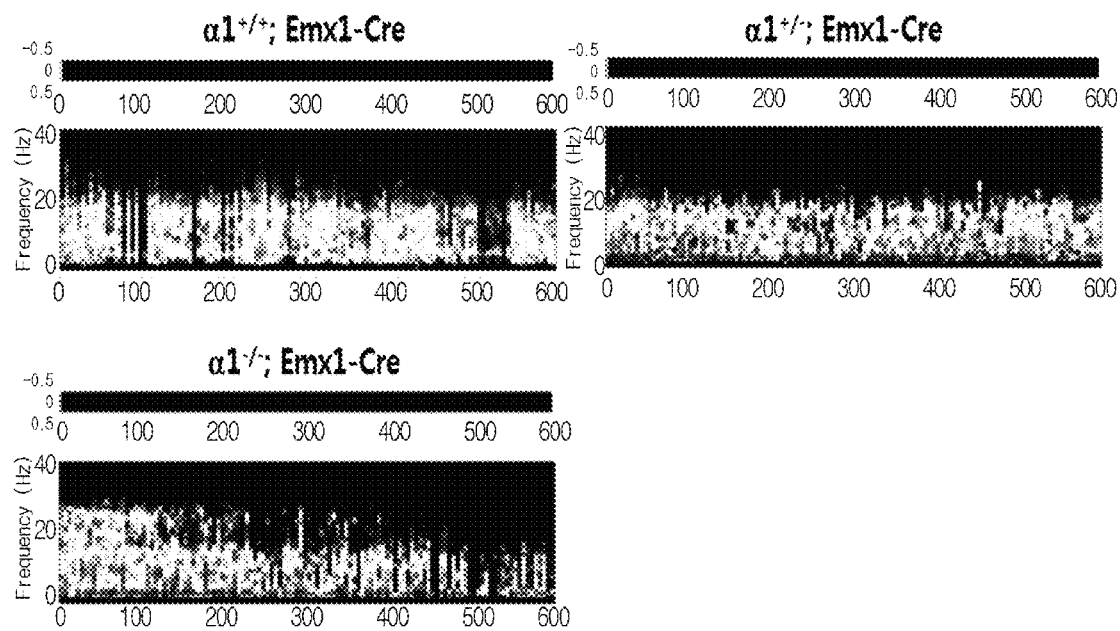

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: GAB2 a1 forward primer

<400> SEQUENCE: 1
tctgcatgtg ggacaaagac                                           20

<210> SEQ ID NO 2
<211> LENGTH: 20
<212> TYPE: DNA
<213> ORGANISM: Artificial Sequence
<220> FEATURE:
<223> OTHER INFORMATION: GAB2 a1 reverse primer

<400> SEQUENCE: 2
acgcataccc tctcttggtg                                           20

<210> SEQ ID NO 3
<211> LENGTH: 22
<212> TYPE: DNA
<213> ORGANISM: Artificial Sequence
<220> FEATURE:
<223> OTHER INFORMATION: GAB2 a1 reverse primer 2

<400> SEQUENCE: 3
tgattgcttt tctgagatag gg                                        22

<210> SEQ ID NO 4
<211> LENGTH: 20
<212> TYPE: DNA
<213> ORGANISM: Artificial Sequence
<220> FEATURE:
<223> OTHER INFORMATION: F1 a1G forward primer

<400> SEQUENCE: 4
atacgtggtt cgagcgagtc                                           20

<210> SEQ ID NO 5
<211> LENGTH: 20
<212> TYPE: DNA
<213> ORGANISM: Artificial Sequence
<220> FEATURE:
<223> OTHER INFORMATION: F1 a1G reverse primer

<400> SEQUENCE: 5
cgaaggcctg acgtagaaag                                           20

<210> SEQ ID NO 6
<211> LENGTH: 22
<212> TYPE: DNA
<213> ORGANISM: Artificial Sequence
<220> FEATURE:
<223> OTHER INFORMATION: PGK22 a1G reverse primer

<400> SEQUENCE: 6
ctgactaggg gaggagtaga ag                                        22

<210> SEQ ID NO 7
<211> LENGTH: 25
<212> TYPE: DNA

```
<213> ORGANISM: Artificial Sequence
<220> FEATURE:
<223> OTHER INFORMATION: Emx1-Cre forward primer

<400> SEQUENCE: 7
acctgatgga catgttcagg gatcg                                              25

<210> SEQ ID NO 8
<211> LENGTH: 25
<212> TYPE: DNA
<213> ORGANISM: Artificial Sequence
<220> FEATURE:
<223> OTHER INFORMATION: Emx1-Cre reverse primer

<400> SEQUENCE: 8
tccggttatt caacttgcac catgc                                              25
```

MOUSE MODELS WITH ENHANCED ESSENTIAL TREMOR AND PREPARATION METHOD THEREOF

CROSS REFERENCE TO RELATED APPLICATION

This patent application claims the benefit of priority from Korean Patent Application No. 10-2009-0031857, filed on Apr. 13, 2009, the contents of which are incorporated herein by reference.

BACKGROUND OF THE INVENTION

1. Field of the Invention

The present disclosure relates to a screening method of therapeutic agents for essential tremor by using a mouse model in which essential tremor (or hand tremor) is enhanced.

2. Description of the Related Art

Essential tremor is a typical disease, showing action tremor or postural tremor. Action tremor or postural tremor refers to a type of tremor aggravated throughout active movement, or during posturing such as "holding a cup" or "stretching the arms forward". On the contrary, a tremor, which worsens when motionless and at rest, refers to resting tremor, and often occurs in Parkinson's disease. Essential tremor is a hereditary disease inherited through autosomal dominant inheritance, and thus tends to have high incidence among the family members of an essential tremor patient. Thus, essential tremor is also called familial tremor. The diagnostic characteristic of essential tremor is that it occurs slightly less frequently but more severely in most cases than physiological tremor during normal physiological activities. However, the tremor can not be easily distinguished from other forms of tremors only by apparent symptoms. As a patient ages, tremors tend to increase in amplitude and decrease in frequency. Tremor may be evident only in the upper extremities, and may occur in the head. When tremor is serious, it may occur in the jaw, lips, tongue, and even in the vocal cords, and tremor in the latter causes the voice to tremble when speaking. Even though essential tremor causes relatively mild symptoms, it varies with each individual and begins with minute tremor in one side or in both sides of the body and progresses slowly. These symptoms occur when there is a change in posture or moving state and are not detected in a stable phase unless the disorder is in an advanced stage. No other neurological disorders related to systemic or neuronal disease are caused. It is easy to diagnose this disorder due to its familial tendency, and tremors can sometimes be temporarily alleviated by consumption of alcohol.

Methods for treating essential tremor are based on the use of drugs. Conventional methods that have been used include drinking alcohol or the intake of an alcohol compound (octanol), and taking inhibitory drugs such as a receptor antagonist of the inhibitory neurotransmitter GABA. Inhibitory drugs such as Primidone or Propranolol as a beta-blocker are primarily used. These drugs exhibit about 60% to about 70% efficacy on patients, but are ineffective at completely eradicating the symptoms. When the efficacy does not satisfy expectations, treatment may introduce a secondary therapeutic agent or a physical operation. However, the receptor antagonist of GABA or alcohol compound can interfere with normal functions of the nervous system in addition to tremor, and moreover causes serious side-effects including sleep induction, etc. Dangerous brain surgeries such as thalamectomy or deep-brain stimulation should only be performed as a last resort. While deep-brain stimulation has recently received increasing attention as a relatively safe and reliably effective method for treating tremor, it is quite costly.

The gamma-aminobutyric acid type A ($GABA_A$) receptor superfamily represents one of the classes of receptors through which the major inhibitory neurotransmitter γ-aminobutyric acid (GABA) acts. Widely, although unequally, distributed throughout the mammalian brain, GABA mediates many of its actions through interaction with the $GABA_A$ receptor, which causes alteration in chloride conductance and membrane polarization. In addition to the neurotransmitter such as GABA, a number of drugs, including the anxiolytic and sedating benzodiazepines, also bind to the receptor. In general, the $GABA_A$ receptor includes a chloride channel that opens in response to GABA, allowing chloride ions to enter the cell. This, in turn, effects a slowing of neuronal activity through hyperpolarization of the cell membrane potential.

$GABA_A$ receptors includes five protein subunits, typically composed of two α subunits, two β subunits and one γ subunit. Each subunit includes α 1-6, β 1-3, and γ 1-3 (Mohler, H. et al, Neuroch. Res, 20, 631-636, 1995). The α 1 subunit of the conventional $GABA_A$ receptor was subjected to a knockout procedure to develop a mouse model ($GABA_A$ receptor $\alpha 1^{-/-}$ mouse; Vicini, S. et al, The Journal of Neuroscience, 21, 3009-3016, 2001) exhibiting essential tremor genetically at 17-22 Hz (Kralic, J. E. et al, The Journal of Clinical Investigation, 115, 774-779, 2005). However, there are limitations in these studies on essential tremor and development of therapeutic agents because the tremor intensities were too weak at an early age.

Voltage-dependent calcium channels play a role in increasing the concentration of calcium in a cell by the activity of neural cells (Tsien, R. W., Annu Rev Physiol 45, 341-358, 1983), and are classified into high-voltage dependent and low-voltage dependent channels according to the voltage dependency (Tsien, R. W. et al, Trends Neurosci, 18, 52-54, 1995). T-type calcium channels are an exemplary low-voltage dependent calcium channel, and there are three kinds of Cav3.1 (α1G), 3.2 (α1H), and 3.3 (α1I) in mammals according to the genotype of α1 subunit. α1G calcium channels are involved in production of burst firings of nerve cells in the thalamic nucleus, and their major pathological functions have been recently revealed (Kim, D. et al., Science, 302, 117-119, 2003; Kim, D. et al., Neuron, 31, 35-45, 2001). The present inventors conventionally disclosed that α1G T-type calcium channel-deficient mice have resistance against essential tremor induced by harmaline, a tremor-inducing agent.

Thus, the present inventors have constructed a double knockout mouse ($\alpha 1^{-/-}$ /$CaV3.1^{-/-}$) by mating a $GABA_A$ receptor $\alpha 1^{-/-}$ mouse which exhibited essential tremor symptoms with an α1G T-type calcium channel knockout mouse which had resistance against essential tremor, studied the essential tremor symptoms of the double knockout mice, observed that the tremor intensity of the double knockout mouse was more severe, unlike that of the conventional $GABA_A$ receptor $\alpha 1^{-/-}$ mouse which failed to meet the expectation that the essential tremor would be improved, enough to be visually confirmed even at an early age, and completed the present invention by confirming that the mouse model may be used as a model for development of therapeutic agents for essential tremor.

The present inventors also have constructed an $\alpha 1^{F/+}$; Emx1-Cre mouse by mating a $GABA_A$ receptor $\alpha 1^{F/F}$ mouse with an Emx1-Cre and constructed an $\alpha 1^{-/-}$; Emx1-Cre by mating the $\alpha 1^{F/+}$/Emx1-Cre mice with each other. The inventors studied the essential tremor symptoms of the conditional knockout mice, observed that the tremor intensity of the $\alpha 1^{-/-}$; Emx1-Cre mouse was more severe than that of the conventional GABA$_A$ receptor α1$^{-/-}$ mouse, and completed the present invention by confirming that the mouse model may be used for the study of essential tremor, for the screening of a drug for essential tremor and as a model for the study of dorsal telencephalon (cortical) functions related to essential tremor.

SUMMARY OF THE INVENTION

One object of the present invention is to provide a GABA$_A$ receptor α1 subunit and T-type Ca$^{2+}$ channel double knockout mouse, exhibiting essential tremor.

Another object of the present invention is to provide a fertilized egg derived from the double knockout mouse.

Still another object of the present invention is to provide a method for constructing the double knockout mouse.

Yet another object of the present invention is to provide a screening method of therapeutic agents for essential tremor by using the double knockout mouse.

In order to achieve the objects, the present invention provides a double knockout mouse (α1$^{-/-}$/CaV3.1$^{-/-}$), in which a GABA$_A$ receptor α1 subunit (α1) and a T-type Ca$^{2+}$ channel (CaV3.1) have been knocked out, exhibiting essential tremor.

The present invention also provides a fertilized egg derived from the double knockout mouse, exhibiting essential tremor.

Furthermore, the present invention provides a method for constructing a double knockout mouse exhibiting essential tremor, including:

1) mating a GABA$_A$ receptor α1 subunit knockout mouse (α1$^{-/-}$) with a T-type Ca$^{2+}$ channel knockout mouse (CaV3.1$^{-/-}$);
2) selecting a mouse that contains the two genes in a heterozygote state among the offspring in Step 1);
3) mating the selected adult α1$^{+/-}$/CaV3.1$^{+/-}$ mice with each other; and
4) selecting a double knockout mouse (α1$^{-/-}$/CaV3.1$^{-/-}$) in which the two genes in Step 1) have all been deficient among the offspring in Step 3).

The present invention also provides a screening method of therapeutic agents for essential tremor, including:

1) administering a test compound to a double knockout mouse (α1$^{-/-}$/CaV3.1$^{-/-}$) exhibiting essential tremor of claim 1;
2) measuring frequencies or tremor intensities when the treated mouse (experimental group) is moving or posturing; and
3) screening the test compound that has decreased the frequencies or tremor intensities compared to mice not treated with the test compound (control group).

The present invention also provides a conditional knockout mouse (α1$^{-/-}$; Emx1-Cre), in which a GABA$_A$ receptor α1 subunit (α1) has been knocked out specifically in dorsal telencephalon, exhibiting essential tremor.

The present invention also provides a fertilized egg derived from the α1$^{-/-}$; Emx1-Cre mouse, exhibiting essential tremor.

The present invention also provides a method for constructing an α1$^{-/-}$; Emx 1-Cre mouse exhibiting essential tremor, comprising the following steps:

1) mating a GABA$_A$ receptor α1 subunit floxed mouse (α1$^{F/F}$) with an Emx1-Cre mouse;
2) Selecting a mouse that contains the GABA$_A$ receptor α1 subunit gene in a heterozygote state and an Emx1-Cre gene, (α1$^{F/+}$; Emx1-Cre) among the offspring in Step 1);
3) mating the selected adult α1$^{F/+}$; Emx1-Cre mice with each other; and
4) selecting a α1$^{-/-}$; Emx1-Cre harboring α1$^{-/-}$ and Emx1-Cre among the offspring in Step 3).

In addition, the present invention provides a screening method of a therapeutic agent for essential tremor, comprising the following steps:

1) administering a test compound to the α1$^{-/-}$; Emx1-Cre mouse exhibiting essential tremor;
2) measuring frequencies or tremor intensities when the treated mouse (experimental group) is moving or posturing; and
3) screening the test compound that has decreased the frequencies or tremor intensities compared to the mouse not treated with the test compound (control group).

BRIEF DESCRIPTION OF THE DRAWINGS

The above and other objects, features and other advantages of the present invention will be more clearly understood from the following detailed description taken in conjunction with the accompanying drawings, in which:

FIG. 1 is a group of photos illustrating results of measured tremor degrees in 30 week-old α1$^{+/+}$/CaV3.1$^{+/+}$ and α1$^{-/-}$/CaV3.1$^{-/-}$ mice by a measurement method using an accelerometer.

FIG. 2 is a group of photos illustrating results of measured tremor degrees in 30 week-old α1$^{+/+}$/CaV3.1$^{+/+}$, α1$^{-/-}$/CaV3.1$^{+/+}$, and α1$^{-/-}$/CaV3.1$^{-/-}$ mice by a measurement method using an accelerometer.

FIG. 3 is a graph illustrating results of measured tremor intensities in 30 week-old α1$^{+/+}$/CaV3.1$^{+/+}$, α1$^{-/-}$/CaV3.1$^{+/+}$, and α1$^{-/-}$/CaV3.1$^{-/-}$ mice by a measurement method using an accelerometer.

FIG. 4 is a graph illustrating results of measured tremor intensities in 20 week-old α 1$^{+/+}$; Emx1-Cre, α1$^{+/-}$; Emx1-Cre, and α1; Emx1-Cre mice by a measurement method using an accelerometer.

DESCRIPTION OF THE PREFERRED EMBODIMENTS

Features and advantages of the present invention will be more clearly understood by the following detailed description of the present preferred embodiments by reference to the accompanying drawings. It is first noted that terms or words used herein should be construed as meanings or concepts corresponding with the technical sprit of the present invention, based on the principle that the inventor can appropriately define the concepts of the terms to best describe his own invention. Also, it should be understood that detailed descriptions of well-known functions and structures related to the present invention will be omitted so as not to unnecessarily obscure the important point of the present invention.

Hereinafter, the present invention will be described in detail.

The present invention provides a double knockout mouse (α1$^{-/-}$/CaV3.1$^{-/-}$), in which a GABA$_A$ receptor α1 subunit (α1) and a T-type Ca$^{2+}$ channel (CaV3.1) have been knocked out, exhibiting essential tremor.

In a specific example of the present invention, a GABA$_A$ receptor α1 subunit knockout mouse (α1$^{-/-}$) was mated with a CaV3.1 channel knockout mouse (CaV3.1$^{-/-}$) to obtain a mouse that contains the two genes in a heterozygote state, and these mice were crossed with each other to yield a mouse (α1$^{-/-}$/CaV3.1$^{-/-}$) in which a GABA$_A$ receptor α1 subunit (α1$^{-/-}$) and a CaV3.1 channel (CaV3.1$^{-/-}$) were doubly knocked out.

The tremor intensities of the double knockout mouse are stronger by at least 3 to 12 folds, preferably 5 to 10 folds than those of a $GABA_A$ receptor α1 subunit knockout mouse.

Furthermore, the tremor intensities may be measured by using an accelerometer.

The present invention also provides a fertilized egg derived from the double knockout mouse, exhibiting essential tremor.

Furthermore, the present invention provides a method for constructing a double knockout mouse exhibiting essential tremor, including:

1) mating a $GABA_A$ receptor α1 subunit knockout mouse (α1$^{-/-}$) with a T-type $Ca^{2+}$ channel knockout mouse (CaV3.1$^{-/-}$);

2) selecting a mouse that contains the two genes in a heterozygote state among the offspring in Step 1);

3) mating the selected adult α1$^{+/-}$/CaV3.1$^{+/-}$ mice with each other; and 4) selecting a double knockout mouse (α1$^{-/-}$/CaV3.1$^{-/-}$) in which the two genes in Step 1) have all been deficient among the offspring in Step 3).

In a specific example of the present invention, a $GABA_A$ receptor α1 subunit knockout mouse (α1$^{-/-}$) was mated with a CaV3.1 channel knockout mouse (CaV3.1$^{-/-}$) to obtain a mouse that contains the two genes in a heterozygote state, and these mice were mated with each other to yield a mouse (α1$^{-/-}$/CaV3.1$^{-/-}$) in which a $GABA_A$ receptor α1 subunit (α1$^{-/-}$) and a CaV3.1 channel (CaV3.1$^{-/-}$) were all knocked out.

In a specific example of the present invention, essential tremors of the α1$^{-/-}$/CaV3.1$^{+/+}$ mice were compared with those of the α1$^{-/-}$/CaV3.1$^{-/-}$ mice to confirm the effects of the knockout of a CaV3.1 channel gene on the α1$^{-/-}$/CaV3.1$^{+/+}$ mice. The analysis results by an accelerometer showed that tremor degrees in α1$^{-/-}$/CaV3.1$^{-/-}$ and α1$^{-/-}$/CaV3.1$^{++}$ mice were measured at 20-25 Hz (See FIG. 2), while tremor intensities in α1$^{-/-}$/CaV3.1$^{-/-}$ mice were stronger by 5 to 10 folds than those in α1$^{-/-}$/CaV3.1$^{+/+}$ and α1$^{+/+}$/CaV3.1$^{+/+}$ (See FIG. 3). The video reading results showed that a weak trembling related to a specific tremor was observed in α1-/-/CaV3.1+/+ mice. Thus, the knockout of a CaV3.1 channel gene has further reinforced the essential tremor by the conventional $GABA_A$ receptor α1 subunit knockout.

The step may additionally include determining whether essential tremor is induced.

The determining method may be performed in a manner to confirm from the video analysis whether the experimental group exhibits unstable postures or severely trembling symptoms during movement or posturing compared to normal mice or in a manner to confirm from the results by an accelerometer whether frequencies and/or tremor intensities have increased. A α1$^{-/-}$/CaV3.1$^{-/-}$ mouse of the present invention exhibits severely trembling symptoms, which have characteristics that the symptoms are not apparent when the mouse is resting, but show up during a postural/kinetic position.

The present invention also provides a screening method of therapeutic agents for essential tremor, including:

1) administering a test compound to a double knockout mouse (α1$^{-/-}$/CaV3.1$^{-/-}$) exhibiting essential tremor;

2) measuring frequencies or tremor intensities when the treated mouse (experimental group) is moving or posturing; and 3) screening the test compound that has decreased the frequencies or tremor intensities compared to mice not treated with the test compound (control group).

The test compound in Step 1) may be any one selected from the group consisting of natural compound, synthetic compound, RNA, DNA, polypeptide, enzyme, protein, ligand, antibody, antigen, metabolic products of bacteria or fungi, and bioactive molecule.

The test compound in Step 1) may be administered to the mouse via oral or parenteral administration. The parenteral administration may be performed by any one method selected from the group consisting of any one injection selected from the group consisting of intradermal, subcutaneous, intravenous, intraperitoneal, and intramuscular injection; rectal injection; local application; patch; and iontophoresis.

Because $GABA_A$ receptor α1$^{-/-}$ mice are disadvantageous in that they have weak tremor intensities and thus should be old enough (>8 months) to have visually-confirmed strong tremulous activity, they are not suitable for use in tremor studies, drug screenings, etc. The α1$^{-/-}$/CaV3.1$^{-/-}$ mice constructed in the present invention exhibits such apparent tremor symptoms even at young ages and strong tremor intensities that the mouse model may be important in overcoming these disadvantages.

The present invention also provides a knockout mouse (α1$^{-/-}$; Emx1-Cre), in which a $GABA_A$ receptor α1 a subunit (α1) has been knocked out specifically in dorsal telencephalon, exhibiting essential tremor.

The present invention also provides a fertilized egg derived from the α1$^{-/-}$; Emx1-Cre mouse, exhibiting essential tremor.

The present inventors constructed a mouse model with reinforced essential tremor by knocking out $GABA_A$ receptor α1 subunit gene specifically in dorsal telencephalon. Particularly, the inventors constructed a knockout mouse (α1$^{-/-}$; Emx1-Cre), in which $GABA_A$ receptor α1 subunit is knocked out specifically in dorsal telencephalon by using Cre-loxP recombinant technique. The constructed α1$^{-/-}$; Emx1-Cre mouse shows tremor symptoms, which have characteristics that the symptoms are not apparent when the mouse is resting, but show up during a postural/kinetic position.

From the result of the analysis by the accelerometer, the present inventors confirmed that the α1$^{-/-}$; Emx1-Cre mouse showed tremor in the frequency of 25-30 Hz, which was similar or 1.5-2 times as strong as that of the $GABA_A$ receptor α1$^{-/-}$ mouse. The tremor was developed much earlier in the mouse (at 3 weeks) than in the $GABA_A$ receptor α1$^{-/-}$ mouse.

Therefore, owing to earlier development and stronger tremor intensity, compared with the $GABA_A$ receptor α1$^{-/-}$ mouse, the α1$^{-/-}$; Emx1-Cre mouse can be effectively used for the study of tremor, screening of a drug for tremor, and as a model for the study of the cerebrum cortex functions related to essential tremor, which has not progressed much, relatively.

The present invention also provides a method for constructing an α1$^{-/-}$; Emx 1-Cre mouse exhibiting essential tremor, comprising the following steps:

mating a $GABA_A$ receptor α1 subunit foxed mouse (α1$^{F/F}$) with a Emx1-Cre mouse;

2) Selecting a mouse that contains the $GABA_A$ receptor α1 subunit gene in a heterozygote state and an Emx1-Cre gene, (α1$^{F/+}$; Emx1-Cre) among the offspring in Step 1);

3) mating the selected adult α1$^{F/+}$; Emx1-Cre mice with each other; and 4) selecting a α1$^{-/-}$; Emx1-Cre mouse harboring α1$^{-/-}$ and Emx1-Cre among the offspring in Step 3).

In addition, the present invention provides a screening method of a therapeutic agent for essential tremor, comprising the following steps:

1) administering a test compound to the α1$^{-/-}$; Emx1-Cre mouse exhibiting essential tremor;

2) measuring frequencies or tremor intensities when the treated mouse (experimental group) is moving or posturing; and 3) screening the test compound that has decreased the frequencies or tremor intensities compared to the mouse not treated with the test compound (control group).

Hereinafter, the present invention will be described in detail with reference to examples.

However, the following examples are provided for illustrative purposes only, and the scope of the present invention should not be limited thereto in any manner.

EXAMPLE 1

Construction and Selection of Double Knockout Mice

<1-1> Construction of $\alpha 1^{-/-}$ Mice and CaV3.1$^{4"}$ Mice

The present inventors obtained GABA$_A$ receptor $\alpha 1^{-/-}$ mice constructed by a method described in the literature (Vicini et al., *The Journal of Neuroscience*. 21, 3009, 2001) from G. Homanics (Department of Anaesthesiology Pharmacology, University of Pittsburgh, Pittsburgh, Pa. 15261, USA).

The present inventors keep CaV3.1 channel knockout mice constructed by a method described in the literature (Kim, D. et al., *Neuron*, 31, 35-45, 2001).

Specifically, mRNA from the brain tissue of a C57BL/6J mouse was subjected to RT-PCR to obtain a rat CaV3.1 cDNA, which was later used as a probe to select a CaV3.1 gene (cacna1G) genome fragment including a CaV3.1 position in the genome library prepared by introduction of cDNA of a 129/sv mouse into a lamdaGT11 vector.

A double selection marker (neo and TK) was inserted into the selected genome to construct a targeting vector including a 11.7 kb homologous fragment. The targeting vector was transduced into a J1 embryonic stem cell line (Dr. R Jeanisch, Whitehead Institute, Cambridge, Mass. 02142, USA. jeanisch@wi.mit.edu). ES clones in which the targeting vector had been transduced were selected by Southern blot analysis and used for construction of a germline chimera. A male germline chimeric mouse was mated with a F1 heterozygous (CaV3.1$^{+/-}$) female C57BL/6J mouse, and then the offspring thereof were mated with each other to construct a homozygous mouse (CaV3.1$^{-/-}$). The genotype of the homozygous mouse was confirmed by PCR.

<1-2> Construction and Selection of $\alpha 1^{-/-}$/CaV3.1$^{4"}$ Double Knockout Mice The GABA$_A$ receptor $\alpha 1$ subunit knockout mouse ($\alpha 1^{-/-}$) was mated with the CaV3.1 channel knockout mouse (CaV3.1$^{-/-}$), and then a genomic PCR was performed using a genomic DNA from the tail of the offspring generated as a template, followed by electrophoresis to identify the genotype. A normal allele was identified for the ca gene by PCR using a primer pair described as SEQ ID No. 1 (5'-TCTG-CATGTGGGACAAAGAC-3') and SEQ ID No. 2 (5'-ACG-CATACCCTCTCTTGGTG-3'), while a normal knockout allele was identified by PCR using a primer pair described as SEQ ID No. 1 and SEQ ID No. 3 (5'-TGATTGCTTTTCT-GAGATAGGG-3'). The PCR was denatured at 95° C. for 5 min and subjected to 29 cycles of 95° C. for 30 sec, 62° C. for 32 sec, and 72° C. for 40 sec and an extension step at 72° C. for 3 min, followed by cooling down at 4° C. A normal allele was identified for the CaV3.1 gene by PCR using a primer pair described as SEQ ID No. 4 (5'-ATACGTGGTTCGAGC-GAGTC-3') and SEQ ID No. 5 (5'-CGAAGGCCTGACGTA-GAAAG-3'), while a knockout allele was identified by PCR using a primer pair described as SEQ ID No. 4 and SEQ ID. 6 (5'-CTGACTAGGGGAGGAGTAGAAG-3'). The PCR was denatured at 94° C. for 5 min and subjected to 40 cycles of 94° C. for 30 sec, 58° C. for 30 sec, and 72° C. for 30 sec and an extension step at 72° C. for 5 min, followed by cooling down at 4° C. The procedures led to a selection of an offspring that contains all the normal and knockout alleles for the al gene and the CaV3.1 gene, respectively. The heterozygotes selected above were mated with each other, and then a genomic PCR was performed in the same manner as above using a genomic DNA from the tail of the offspring generated as a template to select an offspring that contains only knockout alleles for each of the al gene and the CaV3.1 gene as a homozygote.

From the procedure, a double knockout mouse, in which a GABA$_A$ receptor $\alpha 1$ subunit ($\alpha 1^{-/-}$) and a CaV3.1 channel (CaV3.1$^{-/-}$) had been all knocked out, was obtained.

EXAMPLE 2

Measurement of Tremor in an $\alpha 1^{-/-}$/CaV3.1$^{-/-}$ Mouse

In order to analyze tremor symptoms in an $\alpha 1^{-/-}$CaV3.1$^{-/-}$ mouse quantitatively, an accelerometer measurement and a video recording were used. Two 30 week-old $\alpha 1^{-/-}$/CaV3.1$^{-/-}$ mice as an experimental group and two 30 week-old mice ($\alpha 1^{+/+}$/CaV3.1$^{+/+}$) as a control group were used.

An opaque cylinder (diameter 10 cm×height 15 cm) mounted with an accelerometer on the bottom was suspended in the air and used as a measurement platform. A mouse was placed into the cylinder which was allowed to move for measurement of the mouse movement as an electronic signal by the accelerometer. The electronic signal was amplified and recorded to quantitatively determine whether the mouse had tremor, its severities, and frequencies. A video camera was placed on the top of the platform to quantitatively determine in what state (posture, movement, etc.) a mouse exhibited tremor. A mouse was placed into the measurement platform and a record was performed for 10 min by video recording and an accelerometer.

The video analysis showed that the $\alpha 1^{-/-}$/CaV3.1$^{-/-}$ mouse exhibited serious tremor symptoms when it is in an unstable or kinetic posture. On the contrary, the mouse exhibited a very mild or substantially no tremor symptom when it is resting at one place. From the results, it was confirmed that characteristics of the tremor in the $\alpha 1^{-/-}$/CaV3.1$^{-/-}$ mouse qualitatively corresponded to those of essential tremor. On the contrary, no symptom related to tremor was observed at all in a normal mouse.

The analysis by the accelerometer showed that frequencies were measured at less than 5 Hz according to the movement of a normal mouse, as indicated in FIG. 1. On the contrary, frequencies were measured at a range of 20-25 Hz in the $\alpha 1^{-/-/CaV}3.1^{-/-}$ mouse, showing that the record was made specifically at a time range where the mouse had exhibited tremor symptoms, compared to the results from the video reading data. From the results, it was confirmed that the $\alpha 1^{-/-}$/CaV3.1$^{-/-}$ mouse exhibited essential tremor at 20-25 Hz.

EXAMPLE 3

Analysis of Effects of the CaV3.1 Knockout on the $\alpha 1^{-/-}$ mouse

In order to confirm the effects of CaV3.1 channels on essential tremor in a GABA$_A$ receptor $\alpha 1^{-/-}$ mouse, each tremor symptom in a GABA$_A$ receptor $\alpha1^{-/-}$ mouse ($\alpha1^{-/-}$/CaV3.1$^{+/+}$) and an $\alpha1^{-/-}$CaV3.1$^{-/-}$ mouse was measured for comparison. It is known that the tremor symptom in the GABA$_A$ receptor $\alpha1^{-/-}$ mouse is proportional to a mouse's age and evident specifically among 30 week-old mice. Therefore, all the experiments were performed with 30 week-old mice.

Video recordings, and measurements of tremor frequencies and tremor intensities were performed on three 30 week-old normal mice ($\alpha1^{+/+}$/CaV3.1$^{+/+}$) as a control group, four GABA$_A$ receptor $\alpha1$ subunit knockout mouse ($\alpha1^{-/-}$/CaV3.1$^{+/+}$) as the Experimental Group 1, and three double knockout mice ($\alpha1^{-/-}$/CaV3.1$^{-/-}$) as the Experimental Group 2.

The video reading showed that a trembling related to a specific tremor symptom was not observed in the two mouse groups except for the $\alpha1^{-/-}$/CaV3.1$^{-/-}$ group.

The analysis by the accelerometer showed that tremor symptoms were measured at 20-25 Hz only in the $\alpha1^{-/-}$/CaV3.1$^{-/-}$ and $\alpha1^{-/-}$/CaV3.1$^{+/+}$ mice and tremor frequencies in the $\alpha1^{-/-}$/CaV3.1$^{-/-}$ mice were stronger by 5 to 10 folds than those in the $\alpha1^{-/-}$/CaV3.1$^{+/+}$ mice.

EXAMPLE 4

Construction of Mice with Reinforced Essential Tremor by Knocking out GABA$_A$ Receptor $\alpha1$ Subunit Gene Specifically in Dorsal Telencephalon <4-1> Construction of $\alpha1^{-/-}$; Emx1-Cre mice The present inventors obtained GABA$_A$ receptor $\alpha1^{F/F}$ mice constructed by a method described in the literature (Vicini et al., *The Journal of Neuroscience*. Volume 21, p. 3009, May, 2001) from G. Homanics.

The present inventors obtained Emx1-Cre mice constructed by a method described in the literature (Takuji et al., *Genesis*. Volume 38, p. 130, 2004) from Itohara Shigeyoshi.

The present inventors constructed a knockout mouse ($\alpha1^{-/-}$; Emx1-Cre), in which a GABA$_A$ receptor $\alpha1$ subunit ($\alpha1$) has been knocked out specifically in dorsal telencephalon, by using Cre-loxP recombinant technique. Particularly, a GABA$_A$ receptor $\alpha1^{F/F}$ mouse was mated with an Emx1-Cre mouse, and then the offspring ($\alpha1^{F/+}$/Emx1-Cre) thereof were mated with each other to construct a homozygous mouse ($\alpha1^{-/-}$; Emx1-Cre).

<4-2> Construction and Selection of $\alpha1^{-/-}$; Emx1-Cre Mice

The GABA$_A$ receptor $\alpha1$ subunit floxed mouse ($\alpha1^{F/F}$) was mated with the Emx1-Cre transgenic mouse, and then a genomic PCR was performed using a genomic DNA from the tail of the offspring generated as a template, followed by electrophoresis to identify the genotype. A heterozygote gene ($\alpha1^{F/+}$) was identified for the $\alpha1$ gene by PCR using a primer pair described as SEQ ID No. 1 (5'-TCTGCATGTGGGA-CAAAGAC-3') and SEQ ID No. 2 (5'-ACGCATAC-CCTCTCTTGGTG-3'). The PCR was denatured at 95° C. for 5 min and subjected to 29 cycles of 95° C. for 30 sec, 62° C. for 32 sec, and 72° C. for 40 sec and an extension step at 72° C. for 3 min, followed by cooling down at 4° C. A transgenic gene was identified for the Emx1-Cre gene by PCR using a primer pair described as SEQ ID No. 7 (5'-ACCTGATGGA-CATGTTCAGGGATCG-3') and SEQ ID No. 8 (5'-TCCG-GTTATTCAACTTGCACCATGC-3'). The PCR was denatured at 94° C. for 3 min and subjected to 35 cycles of 94° C. for 30 sec, 60° C. for 30 sec, and 72° C. for 60 sec and an extension step at 72° C. for 5 min, followed by cooling down at 4° C. The procedures led to a selection of an offspring ($\alpha1^{F/+}$; Emx1-Cre) that contains all the normal and floxed alleles for the $\alpha1$ gene and the Emx1-Cre transgenic gene, respectively. The heterozygotes selected above were mated with each other, and then a genomic PCR was performed with a primer pair described as SEQ ID No. 1 and SEQ ID No. 3 (5'-TGATTGCTTTTCTGAGATAGGG-3') in the same manner as above using a genomic DNA from the tail of the offspring generated as a template to select an offspring ($\alpha1^{-/-}$; Emx1-Cre) that contains knockout alleles for the ca gene and the Emx1-Cre gene.

From the procedure, a knockout mouse ($\alpha1^{-/-}$; Emx1-Cre), in which a GABA$_A$ receptor $\alpha1$ subunit ($\alpha1^{-/-}$) had been knocked out specifically in dorsal telencephalon, was obtained.

EXAMPLE 5

Measurement of Tremor in an $\alpha1^{-/-}$; Emx1-Cre Mouse

In order to analyze tremor symptoms in an $\alpha1^{-/-}$; Emx1-Cre mouse quantitatively, an accelerometer measurement and a video recording were used. Two 20 week-old $\alpha1^{-/-}$; Emx1-Cre mice as an experimental group and five 20 week-old littermate mice ($\alpha1^{+/+}$; Emx1-Cre or $\alpha1^{+/-}$; Emx1-Cre) as a control group were used.

The video analysis showed that the $\alpha1^{-/-}$; Emx1-Cre mouse exhibited serious tremor symptoms when it is in an unstable or kinetic posture. On the contrary, the mouse exhibited a very mild or substantially no tremor symptom when it is resting at one place. From the results, it was confirmed that characteristics of the tremor in the $\alpha1^{-/-}$; Emx1-Cre mouse qualitatively corresponded to those of essential tremor. On the contrary, no symptom related to tremor was observed at all in a control group. The analysis by the accelerometer showed that frequencies were measured at a range of 25-30 Hz in the $\alpha1^{-/-}$; Emx1-Cre mouse, showing that the record was made specifically at a time range where the mouse had exhibited tremor symptoms, compared to the results from the video reading data. From the results, it was confirmed that the $\alpha1^{-/-}$; Emx1-Cre mouse exhibited essential tremor at 25-30 Hz. The tremor intensity of the $\alpha1^{-/-}$; Emx1-Cre mouse was similar or 1.5-2 times as strong as that of the GABA$_A$ receptor $\alpha1^{-/-}$ mouse. The tremor developed much earlier in the mouse (at 3 weeks) than in the GABA$_A$ receptor $\alpha1^{-/-}$ mouse.

The $\alpha1$/CaV3.1 double knockout mouse or $\alpha1^{-/-}$; Emx1-Cre mouse of the present invention may be usefully used for development of therapeutic agents for essential tremor because the mouse exhibits essential tremor strong and evident enough to be visually confirmed, compared to an $\alpha1$ knockout mouse.

An $\alpha1$/CaV3.1 double knockout mouse or $\alpha1^{-/-}$; Emx1-Cre mouse of the present invention and an use using the same may be usefully used for development of therapeutic agents for essential tremor.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A screening method of identifying a therapeutic agent for essential tremor, comprising:
   a) administering a test compound to a gamma-aminobutyric acid A receptor ($GABA_A$) $\alpha1^{-/-}$; Emx1-Cre homozygous knockout mouse whose genome comprises disruption of both $GABA_A$ $\alpha1$ subunit alleles specifically in dorsal telencephalon exhibiting essential tremor, wherein tremor intensity of the $GABA_A$ $\alpha1^{-/-}$; Emx1-Cre mouse is 1.5- to 2-fold stronger in the frequency of 25-30 Hz than those in a $GABA_A$ $\alpha1^{-/-}$ mouse;
   b) measuring tremor frequency or tremor intensity when the treated mouse (experimental group) is moving or posturing; and
   c) identifying the test compound that has decreased the tremor frequency or tremor intensity compared to a $GABA_A$ $\alpha1^{-/-}$; Emx1-Cre mouse not treated with the test compound (control group) as a therapeutic agent for essential tremor.

2. The method as set forth in claim 1, wherein the test compound in Step a) comprises a compound selected from the group consisting of a natural compound, a synthetic compound, RNA, DNA, a polypeptide, an enzyme, a protein, a ligand, an antibody, an antigen, a metabolic product of bacteria or fungi, and a bioactive molecule.

3. The method as set forth in claim 1, wherein the $GABA_A$ $\alpha1^{-/-}$; Emx1-Cre mouse exhibiting essential tremor is constructed by the method comprising:
   a) mating a $GABA_A$ receptor $\alpha1$ subunit floxed mouse ($\alpha1F/F$) with an Emx1-Cre mouse;
   b) selecting a mouse that contains the $GABA_A$ receptor $\alpha1$ subunit gene in a heterozygote state and an Emx1-Cre gene, ($\alpha1F/+$Emx1-Cre) among the offspring in Step a);
   c) mating the selected adult $\alpha1F/+$/Emx1-Cre mice with each other; and
   d) selecting a $GABA_A$ $\alpha1-/-$ Emx1-Cre mouse harboring $GABA_A$ $\alpha1-/-$ and Emx1-Cre among the offspring in Step c).

* * * * *